United States Patent [19]
Clark, Jr. et al.

[11] Patent Number: 5,333,502
[45] Date of Patent: Aug. 2, 1994

[54] METHOD AND APPARATUS FOR MONITORING THE ENVIRONMENT OF A VESSEL

[75] Inventors: William C. Clark, Jr.; Richard J. Jacko, both of Murrysville Boro, Westmoreland County; Lee W. Burtner, Elizabeth Twp., Allegheny County, all of Pa.

[73] Assignee: Westinghouse Electric Corp., Pittsburgh, Pa.

[21] Appl. No.: 945,788

[22] Filed: Sep. 16, 1992

[51] Int. Cl.$^5$ .............................. G01N 29/04
[52] U.S. Cl. .................... 73/623; 73/61.71; 73/61.75; 73/601; 73/866.5; 324/204; 324/220; 324/226
[58] Field of Search ............... 73/622, 623, 620, 601, 73/866.5, 592, 598, 61.71, 61.75; 376/245, 249, 252; 324/220, 204, 226

[56] References Cited

U.S. PATENT DOCUMENTS

| | | | |
|---|---|---|---|
| 3,550,075 | 10/1968 | Hilchie et al. | 340/15.5 |
| 3,779,070 | 12/1973 | Cushman et al. | 73/432 PS |
| 3,896,674 | 7/1975 | Kolb | 73/866.5 |
| 4,189,944 | 2/1980 | Day et al. | 73/623 |
| 4,388,831 | 6/1983 | Sherman | 73/623 |
| 4,418,574 | 12/1983 | Flournoy | 73/601 |
| 4,706,509 | 11/1987 | Riebel | 73/865.5 |
| 4,855,677 | 8/1989 | Clark, Jr. et al. | 324/238 |
| 4,856,337 | 8/1989 | Metala et al. | 73/601 |
| 4,909,091 | 3/1990 | Ellmann et al. | 73/866.5 |
| 4,955,235 | 9/1990 | Metala et al. | 73/601 |
| 4,992,735 | 2/1991 | Cullen et al. | 324/220 |
| 5,025,215 | 6/1991 | Pirl | 324/220 |
| 5,105,876 | 4/1992 | Burack et al. | 73/866.5 |

*Primary Examiner*—Hezron E. Williams
*Assistant Examiner*—Nashmiya Ashkaf
*Attorney, Agent, or Firm*—Daniel P. Cillo

[57] ABSTRACT

A method for monitoring the environment of a vessel provides a liquid (18) which may contain particles (20) in a vessel having containment walls (12), where a hollow member (26) such as a thin tube is inserted into the liquid near the containment walls, and the hollow member contains in it a robotic device (34), which can travel within the hollow member and which can emit and receive ultrasonic waves and electromagnetic fields, where both of the ultrasonic waves and electric fields can pass through the hollow member (26) to the containment walls (12), where the device: emits and receives low frequency ultrasonic waves to and from the containment walls (12) and high frequency ultrasonic waves to and from any particles (20), and emits electromagnetic fields to the containment walls (12) or their combination, where absorptions and reflections from the hollow member walls and the containment walls, and any particles present are measured and any current generated in the hollow member walls and the containment wall by the electromagnetic fields are measured, and then any differences are measured to determine flaws (24) in the hollow member and containment walls, and properties of any particles (20) in suspension.

12 Claims, 2 Drawing Sheets

METHOD AND APPARATUS FOR MONITORING THE ENVIRONMENT OF A VESSEL

BACKGROUND OF THE INVENTION

Finding an effective way to periodically inspect storage tanks for service induced damage is a continuing problem. In the case of waste storage applications, recent legislative actions have required that these vessels operate reliably over their intended lifetimes. The ability to demonstrate tank integrity for very long times demands reliable diagnostic capabilities. In many cases, corrosion and other forms of environmental degradation in construction materials determine the safe operating life of these vessels. If the precise operating environment of the tank materials are known, the tank can often be designed so that corrosion related failures can be minimized. However, often the operating environment of these storage tanks are not known. The precise solutions inside may change with time and residual solutions from one period of operation may contaminate the solutions added at a subsequent time and result in particularly aggressive environmental conditions for the tank materials. An accurate in-service monitoring system would provide a warning that the corrosion environment of the material has changed. It is important that this warning be recognized sufficiently early that proper corrective or remedial actions can be initiated. The same problems apply to underground pipes.

Additionally, a number of chemical processing, waste remediation and powder manufacturing operations involve the need to carefully assess the mass, density, or percent solids of a liquid slurry in underground pipes or at one or a number of depths in storage tanks, for example, outlets at different depths in the tank, as an important step in production control. Typically, this information is determined from measurements made with samples extracted from the slurry. While this technique can be successful, it is time consuming, after the fact, and not very accurate even when many samples are taken. Further complications arise when it becomes necessary to establish slurry conditions in a tank where the contents are subjected to continuous agitation. Clearly, an on-line, real time, accurate monitoring system is required for enhanced process control.

Unfortunately, it is common practice to bury or encapsulate storage or holding tanks which contain the more toxic or hazardous materials as a liquid or a slurry. Consequently, tank inspection must be accomplished from the inside. This situation is rarely satisfactory since access is limited and the monitoring system often must be protected from the tank environment. A method of detecting cracks and corrosion, as well as assessing particulate properties in a liquid medium in buried storage tanks and piping would be of tremendous value.

In U.S. Pat. No. 3,550,075 (Hilchie et al.), an acoustic transducer was used to detect fractures in casing walls in liquid containing boreholes. In U.S. Pat. No. 4,909,091 (Ellmann et al.), relating to pipe wall faults, a method for the detection of corrosion and pitting in long lengths of pipeline was described. There, a number of ultrasonic sensors were mounted within the circumference of a scraper element of an interior pipeline. The cleaning apparatus directly contacted the pipe being analyzed for corrosion.

A combination pulsing magnetic reluctance coil and ultrasonic transducer, mounted on an instrument that slides along a pipeline wall, or storage tank bottom, has also been used to measure wall thickness and determine the presence of deterioration, as taught in U.S. Pat. No. 4,418,574 (Flournoy). Eddy current probe systems generating a plurality of frequencies to detect flaws at different depths in metallic conduits were taught in U.S. Pat. No. 4,855,677 (Clark, Jr. et al.), and a variety of ultrasonic probe carriers for nondestructive inspection of long lengths of tubes, are also known and taught in U.S. Pat. No. 4,189,944 (Day) and U.S. Pat. No. 4,388,831 (Sherman).

U.S. Pat. Nos. 4,856,337 and 4,955,235 (both Metala et al.) taught a probe carrier system for combined ultrasonic and eddy current inspection of small tubes, primarily metal heat exchanger tubes of steam generators. In these two inventions, the apparatus included a housing which was insertable within the tube to be inspected, and a rotatably mounted probe carrier, where the probes were ultrasonic emitters, and where a pancake eddy current probe was also included for inspection by means of an electromagnetic field. A system for driving such an inspection probe helically within a steam generator tube was taught in U.S. Pat. No. 4,992,735 (Cullen et al.) and U.S. Pat. No. 5,025,215 (Pirl).

In the area of particle concentration measurement, U.S. Pat. No. 4,706,509 (Riebel), taught an apparatus for measuring the concentration of solid particles and particle size distribution in a suspension, by generating ultrasonic waves of several frequencies, where absorption of the waves by various sized particles was measured for each frequency. Similarly, in the area of ore slurries, U.S. Pat. No. 3,779,070 (Cushman et al.), taught transducer emission of two beams of ultrasonic energy, each having different frequencies, through a continuously flowing slurry. Larger particles caused a greater loss or attenuation of the transmitted signals. Changes in attenuation were determined by sensing the amplitude of the ultrasonic signal(s) that had passed through the suspension of particles and comparing it with the known amplitude of the transmitted signal(s) in water.

While these various apparatus solve their individual problems, none provide a simple and economical means to measure slurry or suspension properties while at the same time providing capability to monitor the structural integrity of buried holding tanks containing such slurries, suspensions, or other liquid fluids. What is needed is a dual monitor for checking storage tank damage and slurry or suspension properties, capable of operation in one or the other or both modes. It is one of the main objects of this invention to provide such a combined storage tank damage and particulate suspension properties monitor.

SUMMARY OF THE INVENTION

Accordingly, the invention resides in a method for monitoring the environment of a vessel, characterized by the steps of providing a liquid which may contain particles in suspension disposed in a vessel having containment walls; inserting a hollow member into the contained liquid near the containment walls, where the hollow member has walls with inner and outer sides, and has disposed therein at least one robotic device which can travel within the length of the inserted hollow member and can emit and receive ultrasonic waves and electromagnetic fields, where both the ultrasonic waves and electromagnetic fields can pass through the hollow member and the liquid to the containment walls;

moving the robotic device while emitting and receiving at least one of: low frequency ultrasonic waves which are absorbed and partially reflected by the hollow member walls and the containment walls, high frequency ultrasonic waves which are absorbed and partially reflected by any particles in suspension within the liquid in the vessel, and electromagnetic fields, where the fields emitted are selected so that they permeate the interior of the hollow member walls and the containment walls and cause eddy currents therein and also permeate the liquid and interact with any particles in suspension; measuring the absorptions and reflections of any emitted ultrasonic waves and any eddy currents generated by any emitted electromagnetic fields; and measuring the differences in the absorptions of any emitted and received ultrasonic waves and eddy current differences in any emitted electromagnetic fields; to determine flaws in the hollow member and containment walls, and properties of any particles in suspension.

Preferably, the insertable hollow member is a thin metal tube conformed to be parallel to the inner wall of the container in which it is to be used, where the containment wall is also metal; selected low frequencies are below 3 mHz (3,000,000 cycles per second), and selected high frequencies are above 3 mHz. Advantageously, the hollow member can have welds, preferably opposite the welds in the containment walls, so that flaws measured in the hollow member walls will indicate flaws present or starting to affect the containment walls. This method and apparatus could be used in buried, metal storage tanks made from many welded metal plates and containing hazardous liquid suspensions, and not only safely and inexpensively measure the viscosity of the liquid at various depths, but also the thickness of slime on the inner tank wall, the amount of corrosion on the inner and outer tank wall, the amount of pitting in the tank wall, the remaining thickness of the tank wall, and any cracks in the tank wall, for example, at weld points.

The invention also resides in an apparatus for monitoring the environment of a vessel, characterized in that the apparatus comprises a hollow member having walls through which ultrasonic waves and electromagnetic fields can pass and which is insertable in a liquid disposed in a vessel having containment walls; at least one robotic device, disposed in the hollow member, capable of selectively monitoring at least one of particle properties within a liquid and hollow member and containment wall flaws, where the robotic device can travel within the length of the hollow member and is adapted to selectively emit and receive, through the wall of the hollow member and through a liquid, at least one of ultrasonic waves of a selected low frequency, ultrasonic waves of a selected high frequency, and electromagnetic fields; and a measuring device capable of measuring the difference in the absorptions of any emitted and received ultrasonic waves and electronic fields, and capable of producing output signals effective to determine properties of any particles in liquid suspension and flaws in the hollow member and vessel containment walls.

BRIEF DESCRIPTION OF THE DRAWING

In order that the invention will be more clearly understood, convenient embodiments thereof will now be described, by way of example, with reference to the accompanying drawings, in which.

DESCRIPTION OF THE PREFERRED EMBODIMENTS

Figure 1:
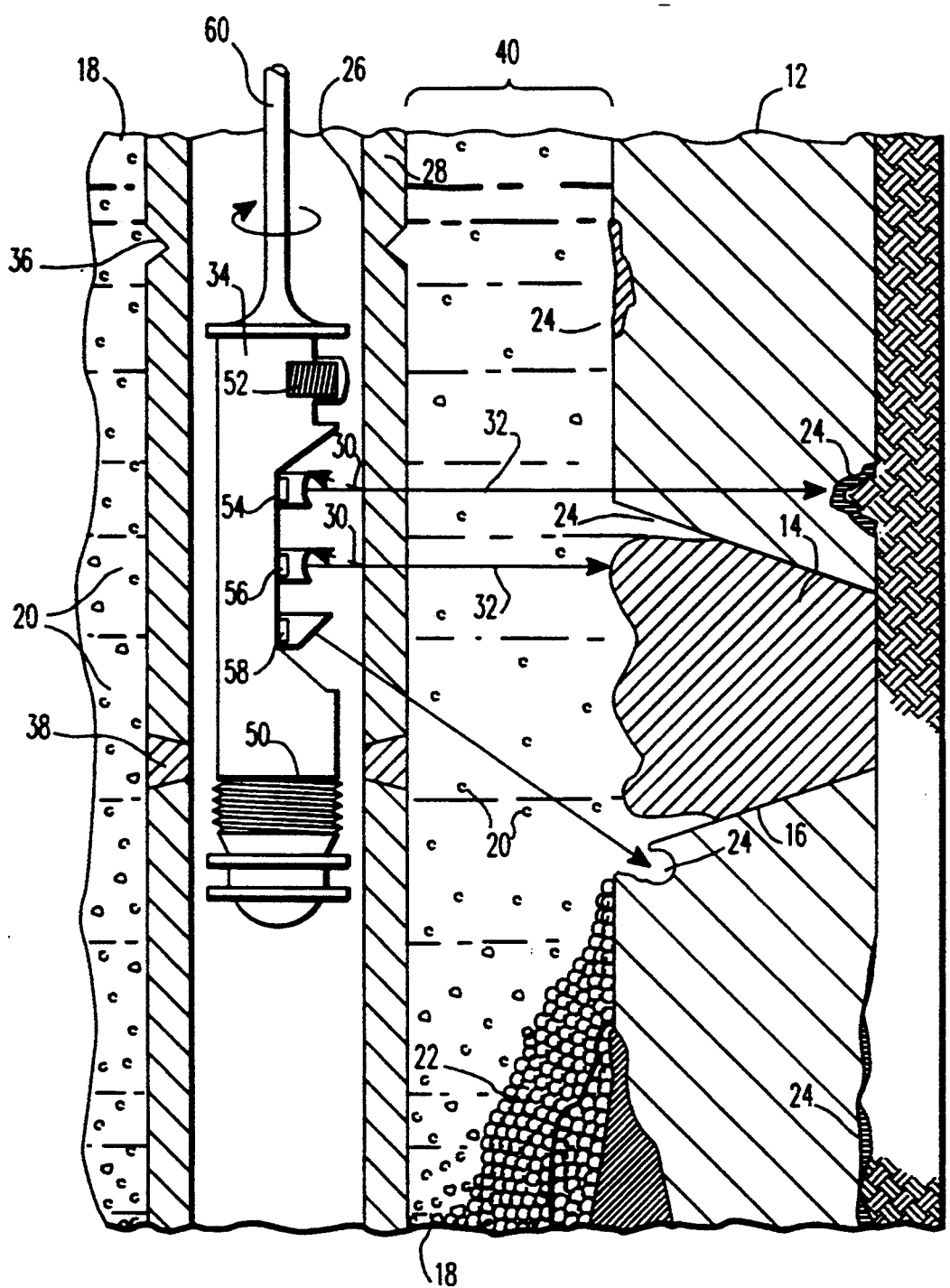
FIG. 1, which best shows the invention, is a view partially in section of an apparatus having a robotic device in place within a hollow tube, submersed in a fluid containing suspended particles next to the wall of a vessel.

Referring now to FIG. 1, a containment wall 12, such as an underground metal pipe or casement, or a buried, metal storage tank wall, is shown. The containment wall can contain many, hundreds perhaps of welds 14 and weld joints 16 between containment wall plates or sections. The diameter of the containment wall can be from about 5 cm to 15 cm for pipe and up to 30 meters or more for storage tanks. Usually, in place, contained liquid 18 is disposed within the containment wall 12 and such liquid 18 may contain particulate material 20. The liquid 18 could be, for example, waste suspension in an underground pipe, or corrosive, toxic or hazardous chemicals in a suspension, or slurry in a storage tank.

Over a period of time the liquid 18, and any particulates 20 therein, as well as materials in the ground, could form corrosive sludge deposits 22 on the containment wall and various forms of corrosion or other degradation, such as, pinholes, cracks, pitting, and the like, shown at points 24, especially at or around any weld 14 or weld joints 16. It may be desirable to locate such degradation. Additionally, the density of any particulates 20 within the liquid 18 may vary as shown. It may be desirable to measure such density at various depths in a storage tank at rest or under flow or agitation, or within selected portions of an underground pipe containing a flow of liquid.

The remotely operated apparatus of this invention is used to monitor the environment of vessels such as the described storage tank or underground pipe walls and any liquid contained therein. The apparatus 10, is made up of a hollow member 26, such as a thin walled metal tube, having a wall portion 28. An axially elongated robotic device 34 can travel within the hollow member 26 and can emit and receive ultrasonic waves and/or electromagnetic fields. The hollow member 26, which is generally tubular, can have a diameter of from about 2 cm to about 12 cm, and is preferably of metal, such as stainless steel, having a thickness up to about 1.5 cm.

It is essential that the hollow member 26 be "nearly transparent" to both ultrasonic waves and electromagnetic fields, that is, while some ultrasonic waves will be reflected from the hollow member wall, as shown by dotted lines 30, and electroamagnetic fields will cause eddy currents in the hollow member wall; a substantial number of ultrasonic waves 32 will pass through the hollow member wall 28, and through the liquid 18 between the hollow member wall 28 and the containment wall 12, to contact the containment wall, and electromagnetic fields will also pass through the hollow member wall and cause eddy currents in the containment wall. For both the ultrasonic and electromagnetic probes, this "transparency" is accomplished through the use of thin wall tubing which has a minimum effect on energy transmission. The inspection tube hollow member 26 wall dimensions are selected in conjunction with the probe parameters including diameter and frequency.

As a very important embodiment, the hollow member 26 can, at selected locations, have notches 36 or the like subject to degradation, or welds 38, and can be permanently positioned in the same environment as the containment wall 12. The liquid 18 would have a similar effect on, for example, the hollow member weld 38 as the containment wall weld 14, usually to a greater degree, and such effects could be monitored by means of the ultrasonic waves 30 reflected from the hollow member walls and used to indicate or predict current or future problems in the containment wall. The notches can be placed at different depths in the liquid 18 and the hollow member welds 38 can be placed opposite containment wall welds 14 for degradation comparison purposes. The distance 40 between the hollow member wall 26 and containment wall 12 for the described monitoring to be effective is in the range of from about 1.5 cm to about 3.0 cm.

The ultrasonic waves from the probes also pass through the liquid in the distance 40, which liquid can contain particulate material. Reflections from each particle will produce an ultrasonic signal that will appear on a time base sweep of an oscilloscope display that would be an integral part of the ultrasonic inspection system. If the spacing 40 between the hollow tube 26 and containment wall target 12 is accurately known, and the time required for the sound beam to travel from the spacing 40 is measured, the sonic velocity can be calculated (from velocity=distance/time) for the slurry or other medium that fills the sampling cavity space 40. From a prior calibration of sonic velocity versus slurry mass (or density) for the specific system under consideration, the density can be established from ultrasonic measurements alone.

Figure 2:
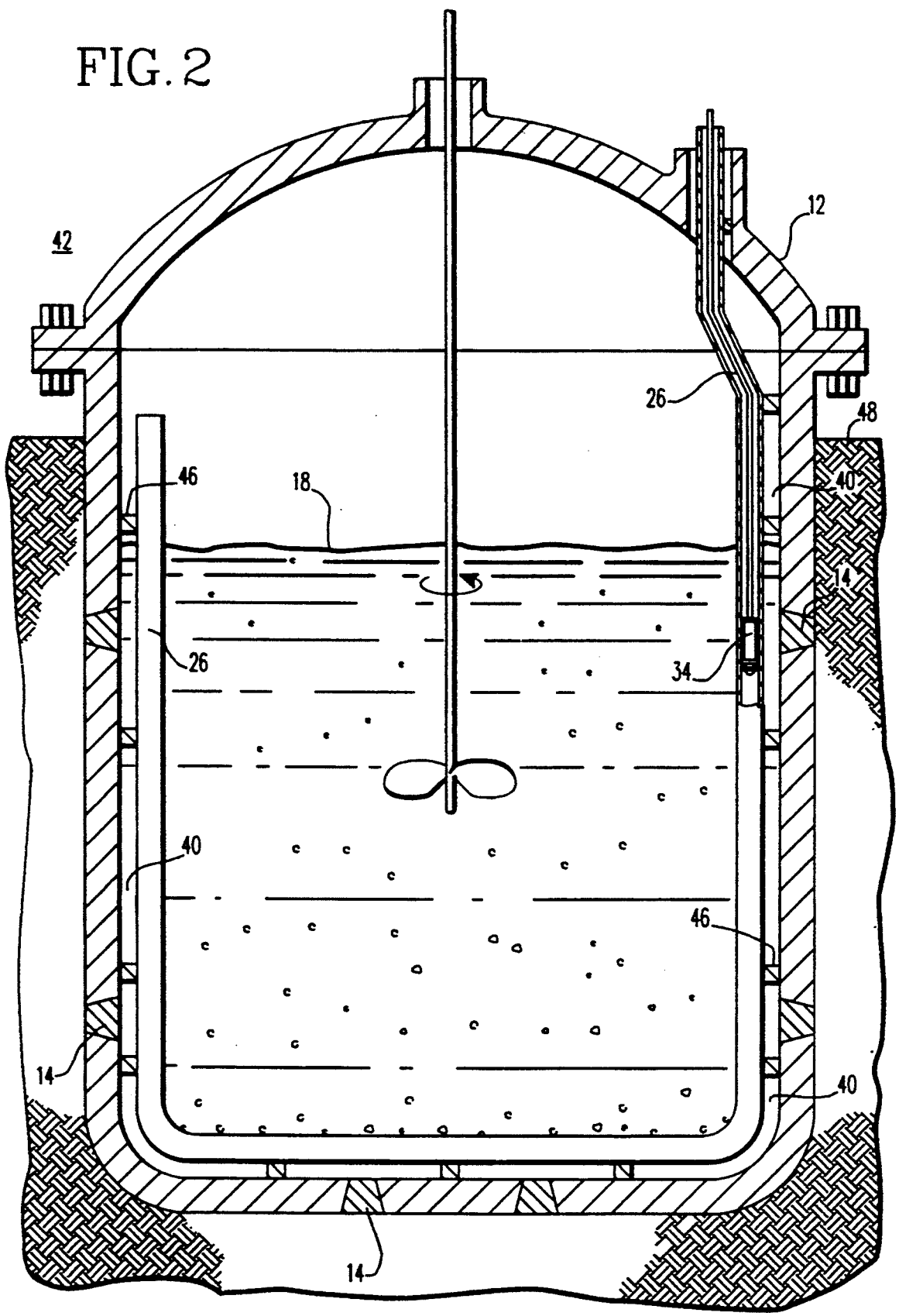
FIG. 2, is a view partially in section of the apparatus of FIG. 1 in place next to the wall of an underground storage tank.

An overall view of such an apparatus 10, with a robotic device 34 in place within a buried storage tank 42 having containment wall 12, is shown in FIG. 2. The weld sections are shown as 14 and the slurry 18 is shown in agitation caused by stirrer 44. The density of the particulate matter in the slurry is shown as increasing with depth. The hollow member 26, containing the robotic device 34, is held in place within the tank 42 by supports 46, which may be a metal brace welded to the containment wall 12. In a situation such as shown in FIG. 2, it may be important to know the slurry density at the bottom of the tank in order to determine how much stirring is needed to keep the particles from settling. It may also be important to monitor the condition of the welds and tank wall to prevent slurry leakage into the soil 48.

The robotic device can selectively monitor both the particle properties within the liquid 18, and containment wall flaws, as it travels within the length of the inserted hollow member 26. The means to allow such monitoring would be the selective use of at least one of emission and reception of ultrasonic waves and the emission and reception of electromagnetic fields, so that ultrasonic waves and electromagnetic fields can be used alone or together, to monitor the environment. By measuring the differences in the absorptions of any emitted and received ultrasonic waves and differences in any emitted electromagnetic fields, by, for example a computer, flaws in the containment walls and properties of any particles in suspension can be measured at any point along the length of inserted tube 16.

The robotic device 34 can be a carrier for probes 50, 52, 54, 56 and 58 which can be used alone or in any combination. The robotic device 34 would be rotatably mounted onto a main housing assembly that is inserted within the tube 26. The housing assembly would have one end which remains stationary during operation of the robotic device and an other end, which includes a cable housing proximate to the robotic device, which would rotate and advance or retract axially during operation. The cable housing would be connected to the robotic device by means of driving mechanism connection 60, and serves to move the sampling device along a helical path, as is well known in the art. Usually, a clear couplant or cooling fluid medium not containing any particulate matter, such as water or an aqueous solution, is present inside the hollow member 26 while the robotic device is in use. The couplant is supplied by a variety of techniques well known in the art.

The probes can include, for example a bobbin eddy current probe 50 which winds around the circumference of the robotic device 34, somewhat as shown in FIG. 1, and a spring loaded, surface riding, pancake eddy current probe 52, which is usually smaller and wound transverse to the axis of the robotic device 34. These probes could be operated, preferably, in the range of from 1 $kH_Z$ to 5 $mH_Z$. One or more of these types of eddy current probes can be utilized, of various diameters, to emit various frequencies to detect defects at various depths within the containment wall 12.

This probe combination would serve as an inspection and diagnostic device. Both of these probes utilize emission of an electromagnetic field, which is received and then recorded by an associated computer means, to scan the tube containment wall 12 and welds 14 for any defects. Both probes would usually be encased in self-lubricating plastic to protect the delicate coil windings and minimize any friction with the inside of the hollow member 26. The bobbin probe 50 provides generalized information about containment wall and weld defects and the pancake probe 52 provides much more concentrated electromagnetic emissions which allows a more exact location of the flawed areas.

Each of the eddy current probes 50 and 52 are connected by way of cable and then lead wire to an external eddy current tester means, the output of which is connected to the input of an associated computer and the input of which is connected to the output of the computer in order to interpret signals associated with the electromagnetic fields. Electromagnetic alternating fields could be introduced into the containment wall 12, and with respect to amplitude could be detected at a distance from the introduction point and the phase displacement measured, to identify defects in the containment wall in order to interpret signals associated with the electromagnetic fields.

Alternating current conducted through the eddy current coil causes the coil to emanate a time-varying magnetic field which in turn induces eddy currents in the inner walls of the containment wall 12 and weld portion 14 as the coil is moved axially. Because the eddy currents create a magnetic field that is opposite in polarity to the time-varying magnetic field emanated by the probe coil, the eddy currents generated in the containment wall 12 and welds 14 apply a measurable impedance to the alternating current that fluctuates through the coil. Since defects in the containment wall 12 or welds 14 create regions of variable resistance, eddy current probes may be used to locate defects by constantly monitoring the impedances of the coils as the probe coils are moved along the containment wall. Eddy current coils can also interact with any conducting or magnetic particles in suspension in the liquid 18 allowing measurement of electromagnetic properties, such as magnetic permeability and conductivity of the slurry, critical parameters in many storage tank concerns. A more complete description of such probes, and computer connections associated therewith can be found in U.S. Pat. No. 4,855,677, herein incorporated by reference.

Additionally, a variety of transducer shapes 54, 56 and 58, located at the central axis of the robotic device or offset a predetermined distance from the central axis, can be used as ultrasonic probes on the robotic device, to, if desired, direct ultrasonic beams radially, chordally or axially from the robotic device, which radiated ultrasonic beams would be refracted from particles in space 40 and from containment wall 12, and received by an appropriate device to generate data, as is well known in the art. These probes could be operated preferably, in the range of from 1 mHz to 25 mHz.

As mentioned previously, each of the ultrasonic probes 54, 56, and 58 can be used alone or in combination. They can be used to find defects in the containment wall 12 or to measure slurry density in the sampling cavity 40. Ultrasonic probes are in most ways superior to eddy current probes in measuring both slurry density and wall defects, but they cannot measure the electromagnetic properties of slurries as can eddy current probes, as pointed out previously. When it is desired to use ultrasonics to determine slurry density, the ultrasonic probes are operated at a frequency of from about 3 mHz to 25 mHz. When it is desired to determine wall defects the ultrasonic probes are operated at a frequency of from about 1 mHz to 3 mHz, that is lower than for slurry use.

These ultrasonic probes would each be connected to individual ultrasonic pulser receiver means by a cable. The outputs of these pulser receivers would be connected to the input side of the associated computer and the inputs connected to the output of the computer in order to interpret signals associated with the ultrasonic waves. An ultrasonic signal could be emitted and then reflected from the containment wall 12, and the time delay difference converted to a test signal for wall thickness, allowing a determination if wall thickness has been reduced due to corrosion and/or pitting. A more complete description of such probes, their operation, and computer connections associated therewith can be found in U.S. Pat. No. 4,856,337, herein incorporated by reference.

The driving mechanism to move the robotic device into the hollow tube 26, rotationally within the length of the tube and out of the tube includes a motor connected to a source of electrical power and can have a helical drive train within the housing assembly mentioned previously, which can be used for imparting a rotational movement, generally about 30° depending on the number of probe means on the sampling device, in order to properly scan the containment wall surface of the tube. The rotation can be a helical or screw-wise motion, or ±30° rotation about the central axis of the tube. This rotation is imparted to the cable housing which is connected to the robotic device. Thus, the robotic device is usually rotatably mounted on and helically movable with respect to the driving mechanism. The helical drive train can be formed from a colinear arrangement of an electric motor, a gearbox, and an optical encoder. Shaft couplings can connect the input shaft of the optical encoder to the output shaft of the gearbox, and the output shaft of the encoder to the input shaft of a slip ring. The slip ring could allow the ultrasonic and eddy current probes to be connected to their various power sources despite the relative rotary movement between these probes, and the stationary drive train housing.

Optionally, slip rings, which sometimes pose reliability problems, could be eliminated if a back and forth rotation about the central axis of the tube is utilized rather than full continuous, screw type rotation. A variety of such driving mechanisms for tube sampling devices are well known in the art and further details with regard thereto can be found in U.S. Pat. No. 4,856,337, herein incorporated by reference.

As an example of operation, a process of monitoring the environment of a vessel, such as a metallic, underground storage tank would include: providing a toxic particulate slurry within containment walls—step (A), inserting a hollow metal tube into the slurry, where the tube has inner and outer side walls and contains a robotic device which can travel the length of the metal tube, where the robotic device can selectively emit and receive ultrasonic waves, or electromagnetic fields, or both, and where the waves or fields can pass through the metal tube to the containment wall-step (B), moving the robotic device while emitting and receiving low and/or high frequency ultrasonic waves, and/or electromagnetic fields, where the low frequency waves and the electromagnetic field cause currents in the containment wall and the high frequency waves and absorbed and partially reflected by particles in the slurry—step (C), measuring all absorptions and reflections—step (D), and measuring the differences in the absorptions and reflections to determine flaws in the hollow member and containment walls and properties of any particles in suspension—step (E).

We claim:

1. A method for monitoring the environment of a vessel comprising the steps:

A) providing a liquid which may contain particles in suspension disposed in a vessel having containment walls;

B) inserting a hollow member into the contained liquid near the containment walls, where the hollow member has walls with inner and outer sides, and has disposed therein at least one robotic device which can travel within the length of the inserted hollow member and can emit and receive ultrasonic waves and electromagnetic fields, where both the ultrasonic waves and electromagnetic fields can pass through the hollow member and the liquid to the containment walls;

C) moving the robotic device while emitting and receiving at least one of:

i) low frequency ultrasonic waves, which are absorbed and partially reflected by the hollow member walls and the containment walls, ii) high frequency ultrasonic waves, which are absorbed and partially reflected by any particles in suspension within the liquid in the vessel, and iii) electromagnetic fields, where the fields emitted are selected so that they permeate the interior of the hollow member walls and the containment walls and cause eddy currents therein and also permeate the liquid and interact with any conducting or magnetic particles in suspension;

D) measuring i) the absorptions and reflections of any emitted ultrasonic waves and
ii) any eddy currents generated by any emitted electromagnetic fields, and E) measuring
i) the differences in the absorptions of any emitted and received ultrasonic wave and
ii) eddy current differences in any emitted electromagnetic fields;
to determine flaws in the hollow member and containment walls, and properties of any particles in suspension.

2. The method of claim 1, where the liquid contains a suspension of particles, the hollow member is a metal tube having a thickness up to 1.5 cm, the density of the particles in suspension is measured, and the permeability and conductivity of the particles in suspension are measured.

3. The method of claim 1, where the hollow member is a metal tube and contains at least one of welds and notches subject to degradation.

4. The method of claim 1, where containment walls are of welded metal plate, the hollow member is metal, has welds opposite welds in the containment walls subject to degradation, and measurements flaws in the hollow member are used to indicate flaws in the containment walls.

5. The method for claim 1, where low frequency ultrasonic waves have a frequency up to 3 mHz, and where the high frequency ultrasonic waves have a frequency over 3 mHz.

6. The method of claim 1, where the robotic device is moved by means of a driving mechanism, where the robotic device is rotatably mounted on the driving mechanism, and an associated computer interprets signals associated with the electromagnetic fields or ultrasonic waves.

7. The method of claim 1, wherein the liquid is a suspension containing particles and the vessel is a buried metal storage tank.

8. An apparatus for monitoring the environment of a vessel, characterized in that the apparatus comprises:
A) a hollow member having walls through which ultrasonic waves and electromagnetic fields can pass and which is insertable in a liquid disposed in a vessel having containment walls,
B) at least one robotic device disposed in the hollow member, said device having means for selectively monitoring at least one of: properties of the contained liquid, and hollow member and containment wall flaws, where the robotic device can travel within the length of the hollow member and is adapted to selectively emit and receive, through the wall of the hollow member and through the liquid, at least one of ultrasonic waves of a selected low frequency, ultrasonic waves of a selected high frequency, and electromagnetic fields,
C) a measuring device capable of measuring the differences in the absorptions of any emitted and received ultrasonic waves and electromagnetic fields; and capable of producing output signals effective to determine properties of any particles in liquid suspension and flaws in the hollow member and vessel containment walls.

9. The apparatus of claim 8, where the hollow member is a metal tube and contains at least one of welds and notches subject to degradation and the vessel containment wall contains welds.

10. The apparatus of claim 9, where the hollow member is a metal tube having a thickness up to 1.5 cm, and has welds which when inserted into a vessel will be opposite welds in the vessel containment wall, and has notches subject to degradation when inserted in the liquid.

11. The apparatus of claim 8, where the hollow member contains a fluid couplant medium.

12. The apparatus of claim 8, where the robotic device can emit and receive ultrasonic waves and electromagnetic fields.

* * * * *